United States Patent

Blais

[11] Patent Number: 5,827,661
[45] Date of Patent: Oct. 27, 1998

[54] ENHANCING DETECTION POLYMERASE CHAIN REACTION ASSAYS BY RNA TRANSCRIPTION AND IMMUNODETECTION OF RNA:DNA HYBRIDS

[75] Inventor: Burton W. Blais, Finch, Canada

[73] Assignee: Kalyx Biosciences Incorporated, Ottawa, Canada

[21] Appl. No.: 718,596

[22] Filed: Sep. 23, 1996

Related U.S. Application Data

[63] Continuation of Ser. No. 366,619, Dec. 30, 1994, abandoned.

[30] Foreign Application Priority Data

Dec. 23, 1994 [CA] Canada ................................. 2137070

[51] Int. Cl.$^6$ .......................... C12Q 1/68; G01N 33/53; C12P 19/34; C07H 21/04
[52] U.S. Cl. .............................. 435/6; 435/71; 435/91.1; 435/91.2; 536/243; 536/245
[58] Field of Search ............................ 435/6, 91.1, 91.2, 435/7.1; 536/24.3, 21.31, 24.32, 24.33, 24.5; 530/387.1, 388.1

[56] References Cited

U.S. PATENT DOCUMENTS

| | | | |
|---|---|---|---|
| 4,683,105 | 7/1987 | Hager | 376/259 |
| 4,683,202 | 7/1987 | Mullis | 435/91 |
| 4,833,084 | 5/1989 | Carrico | 435/240.27 |
| 5,130,238 | 7/1992 | Malek et al. | 435/91 |
| 5,166,051 | 11/1992 | Killeen et al. | 435/7.1 |
| 5,215,899 | 6/1993 | Dattagupta | 435/6 |
| 5,399,491 | 3/1995 | Kacian et al. | 435/91.21 |
| 5,409,818 | 4/1995 | Davey et al. | 435/91.21 |

OTHER PUBLICATIONS

Matthews et al, "Analytical strategies for the use of DNA probes", Anal. Biochem. 169:1–25, 1988.

Gyllensten (1989), "PCR and DNA Sequencing," *Biotechniques*, vol. 7, pp. 700–706.

Lizardi et al. (1988), "Exponential Amplification of Recombinant–RNA Hybridization Probes," *Biotechnology*, vol. 6, pp. 1197–1202.

(List continued on next page.)

*Primary Examiner*—W. Gary Jones
*Assistant Examiner*—Jeffrey Fredman
*Attorney, Agent, or Firm*—McDonnell Boehnen Hulbert & Berghoff

[57] ABSTRACT

This invention relates to a new and novel method for significantly enhancing the sensitivity of assays aimed at detecting the presence of target deoxyribonucleic acid (DNA) or ribonucleic acid (RNA) sequences in a sample. Specifically, this method applies to techniques that employ polymerase chain reactions (PCR®) or other nucleic amplification techniques to amplify copies of the target DNA or RNA (via reverse-transcriptase followed by PCR, Murakawa et al. 1988 DNA 7–287) to allow for detection. The method of the present invention combines the following four steps for the first time: DNA amplicon synthesis and amplification in a modified nucleic acid amplification technique (eg. PCR) using a target nucleic acid sequence as a template; amplicon transcription into RNA sequences with amplification thereof to generate a significantly increased number complementary RNA sequences (i.e., transcriptional enhancement (TE) products); capture of TE products using immobilized complementary DNA sequences; and immunochemical detection of the heteroduplex nucleic acid sequences thereby formed. This method extends standard nucleic acid amplification techniques to accommodate transcription of the PCR products into RNA sequences with amplification, to significantly magnify the signal-to-noise ratio of the diagnostic test This combination of steps results in a new assay with increased simplicity, speed and sensitivity compared to standard nucleic acid detection methods.

6 Claims, 3 Drawing Sheets

OTHER PUBLICATIONS

Watson et al. (1983), *Recombinant DNA*, 2$^{nd}$ ed. (New York: Freeman and Company, pp. 79–80.

Stollar et al. (1987), "Immunochemical Approaches to Gene Probe Assays," *Analytical Biochemistry*, vol. 161, pp. 387–394.

Kitagawa et al. (1982), Comparison of Poly(A) Poly(dT) and Poly(I)Poly(dC) as Immunogens for the Induction of Antibodies to RNA–DNA Hybrids, vol. 19, pp. 413–420.

Fliss et al. (1995), "Multiplex Riboprobes for the Detection of Virulent *Yersinia enterocolitica* and Simple Methods for Their Preparation," vol. 79, pp. 195–202.

Fliss et al. (1993), "Production and Characterization of Anti–DNA–RNA Monoclonal Antibodies and Their Application in *Listeria* Detection," vol. 59, pp. 2698–2705.

Coutlee et al, (1990), "Enzyme Immunoassay for detection of hybrids between PCR–Amplified HIV–1 DNA and a RNA probe: PCR–EIA", Aids Res. Hum. Retro. 6(6):775–784.

Murakawa et al, (1988), "Direct detection of HIV–1 RNA from AIDS and ARC patient samples", DNA 7(4):287–295.

Blais, (Jan. 1994), "Transcriptional enhancement of the *Listeria monocytogenes* PCR and simple immunoenzymatic assay of the product using anti–RNA:DNA antibodies", Appl. Env. Microbiol. 60(1) 348–52.

Young et al, (1991), "Transcription of cRNA for In situ hybridization from polymerase chain reaction–amplified DNA", Lab. Invest. 64(5):709–712.

Blais et al, (1993), "A simple RNA probe system for analysis of *Listeria monocytogenes* polymerase chain reaction products", Appl. Env. Microbiol. 59(9) 2795–2800.

Veelken et al, (1991), "Sensitive detection of clonal antigen receptor gene rearrangements for the diagnosis and monitoring of lymphoid neoplasms by a polymerase chain reaction–mediated ribonuclease protection assay", Blood 78(5):1318–1326.

Coutlee et al, (1989), "Immunodetection of DNA with biotinylated RNA probes: a study of reactivity of a monoclonal antibody to DNA–RNA hybrids", Analy. Biochem. 181:96–105.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: Misc_feature
        ( B ) LOCATION: 1..21
        ( D ) OTHER INFORMATION: primer A     ( x i ) SEQUENCE DESCRIPTION: SEQ ID NO:1:

CATTAGTGGA AAGATGGAAT G                                              21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: misc_feature
        ( B ) LOCATION: 1..20
        ( D ) OTHER INFORMATION: primer B     ( x i ) SEQUENCE DESCRIPTION: SEQ ID NO:2:

GTATCCTCCA GAGTGATCGA                                              20

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: misc_feature
        ( B ) LOCATION: 1..47
        ( D ) OTHER INFORMATION: primer A- T7

( x i ) SEQUENCE DESCRIPTION: SEQ ID NO:3:

AATTTAATAC GACTCACTAT AGGGATCATT AGTGGAAAGA TGGAATG            47

ENHANCING DETECTION POLYMERASE CHAIN REACTION ASSAYS BY RNA TRANSCRIPTION AND IMMUNODETECTION OF RNA:DNA HYBRIDS

This application is a continuation of U.S. patent application Ser. No. 08/366,619, filed Dec. 30, 1994 now abandoned.

BACKGROUND OF THE INVENTION

The present invention relates to improved methods of detecting specific nucleic acid sequences. Examples of nucleic acid sequences are deoxyribonucleic acid (DNA) and ribonucleic acid (RNA) sequences. The molecular subunits of both DNA and RNA are called nucleotides which are linked together to form long polynucleotide chains. Each nucleotide subunit is made of a sugar moiety, a phosphate moiety and a base moiety. It is the sequential ordering of the base moieties [adenine (A), cytosine (C), guanine (G), thymine (T), uracil (U)] that contains DNA or RNA's genetic information. The ordering of these base moieties in a polynucleotide chain and the tendency of the bases to attract and bond with other specific base moieties, is exploited by this invention to locate, detect and isolate specific DNA or RNA sequences.

DNA normally contains two polynucleotide strands twisted about one another lengthwise in a helical manner resembling a ladder where the sides are made of identical sugar (deoxyribose) and phosphate molecules while the rungs are made up of bases extending out from each strand, held together by weak attractive forces. In DNA, the base thymine on one strand always pairs with the base adenine on the opposing strand, and the base guanine always pairs with the base cytosine. This is called complementary base pairing.

RNA is also a polynucleotide strand. However, the sugar moiety is ribose (versus deoxyribose in DNA) and the bases are adenine, guanine, cytosine and uracil. In RNA, the base uracil on one strand can pair with the base adenine on the opposing strand, and the base guanine can pair with the base cytosine. Although RNA can pair with either a complementary strand of RNA or DNA, it is normally single stranded so does not form a helical structure.

Techniques for detecting and/or isolating particular nucleic acid sequences of interest have increased in popularity during recent years especially in terms of application for detecting the presence of the DNA or RNA within pathogens such as viruses, bacteria, or other microorganisms and therefore the presence of these pathogens themselves. These techniques can also be used for other purposes such as to screen bacteria for antibiotic resistance, to aid in the diagnosis of genetic disorders (for example in sickle cell anaemia and thalassaemia), and to detect cancerous cells. Several applications have been developed for the microbiological analysis of clinical, food, environmental, and forensic samples. A general review of a technique and its present and future significance is provided in Biotechnology (August 1983), pp. 471–478 which is incorporated herein by reference.

One situation in which it is desired to detect the presence of target nucleic acids involves the detection of pathogens by means of diagnostic tests which claims a large share of the health care market and the agri-food industry. The definitive identification of microbial pathogens in agricultural commodities (e.g., foods) and clinical specimens requires the observation of the infectious agents or their components, such as specific antigens or nucleic acid (DNA or RNA) sequences. The traditional culture methods for the detection of pathogens are slow, expensive and labour-intensive.

To overcome these disadvantages, simple and rapid methods exploiting new technologies have been developed for detecting the presence of pathogens of medical, environmental and agricultural importance which appear in sample matrices (e.g., foods) at very low concentrations. Several immunological tests are now available which exploit the specificity of the antibody-antigen reaction, namely, agglutination tests, immunofluorescence tests and immunoassays (e.g., radioimmunoassays, enzyme immunoassays).

Radioimmunoassay employs a radioactive isotope as the label. Because of the inconvenience, hazard and difficulty of handling radioactive materials, assay systems have been devised using labels other than radioisotopes as the label component, including enzymes, bacteriophages, metals and organo-metallic complexes, co-enzymes, enzyme substrates, enzyme activators and inhibitors, chemiluminescent reactants, fluorescent molecules, and others.

Enzyme immunoassays use enzyme-labelled immunoreagents (antibodies or antigens) for detection of antigens or antibodies captured on a solid phase. In this technique, enzymes (e.g., peroxidase, alkaline phosphatase) are covalently linked to a detector immunoreagent (e.g., an antigen-specific antibody) by using a cross-linking agent, such as glutaraldehyde, or a procedure such as periodate oxidation. Adsorption onto an easily recoverable solid phase provides for a simple and rapid means of immobilization of immunoreagents for the subsequent capture of antigens or antibodies from a test sample. Since antibodies and antigens contain hydrophobic regions in their structures, they bind readily to hydrophobic surfaces. Most commonly used enzyme immunoassays depend on the adsorption of immunoreagents onto either a flat solid phase, a microporous surface, or a macroporous surface such as polyester cloth. Solid phases, e.g., microtiter plates, tubes or beads, and plastics, e.g., polystyrene, polyvinyl chloride, nylon and polymethacrylate have been commonly used.

Another approach commonly used for pathogen detection involves the use of a nucleic acid probe (DNA or RNA) labelled with a detector moiety (e.g., radioisotope, chemical label such as digoxigenin or biotin, enzymes, fluorescent markers, etc.), which can be hybridized with pathogen-specific nucleic acid sequences immobilized on a solid phase (e.g., membrane or microtiter plate). The hybridized probe is then measured by detecting the presence of the detector moiety.

Yet another more recently developed approach for detecting pathogens involves the use of polymerase chain reaction (PCR), described in U.S. Pat. Nos. 4,683,195 and 4,683,202, for the amplification of unique nucleic acid sequences of bacteria and other target cells (Saiki et al., 1988, Science, 239:487–491). The advantages and limitations of this technique have been reviewed by Gyllensten (Biotechniques 7, 700–706, 1989, incorporated herein by reference). This powerful technique, which uses oligonucleotide primers targeting specific nucleotide sequences of genes, can achieve tremendous amplification of very low numbers of target nucleic acids to levels which can be easily visualized by electrophoretic analysis or by hybridization with a DNA probe.

The amplification of specific DNA sequences by the PCR technique has been widely applied to the rapid and sensitive detection of bacterial pathogens. Although PCR has great potential as a very sensitive and specific technique, in some instances permitting the detection of less than 10 cells (e.g., enterotoxigenic *E. coli*) per reaction, it has not always been possible to achieve this level of sensitivity in its application to the detection of pathogens directly or in enrichment cultures of food and environmental samples. Limitations on the detectability of PCR may in part be due to the presence of inhibitors in the enrichment broth and sample matrix, and other more mundane possibilities such as the quality of the Taq DNA polymerase used and the limited volume of sample (e.g., a few microliters) which can be introduced into the PCR mixture.

The sensitivity of the PCR can be enhanced by detection of the product using DNA probes targeting the amplified sequences (Holstrom et al., 1993, Anal. Biochem., 209:278–283). However, such methods usually involve labour-intensive DNA—DNA hybridization procedures and require the use of probes labelled with detectable chemical or radioactive moieties, which can be costly to prepare and difficult to standardize. Furthermore, DNA probes targeting the PCR product sometimes only produce a moderate improvement in the sensitivity of the test, which may still require more than ten to several hundred cells per reaction in order to give a detectable signal.

Another strategy for signal amplification entails targeting RNA versus DNA. An example of target amplification entails assaying for ribosomal RNA (rRNA) of a microorganism rather than chromosomal DNA. Since rRNA is present in any given cell at $10^4$ times higher concentration than DNA, the number of possible target sequences increases, thereby increasing the probability of detecting the target organism.

Yet another transcription-based amplification system utilising φβ-replicase can produce a 2–5 million-fold amplification of a given target after 4 cycles (Lizardi et al., Biotechnology 6, 1197–1202, 1988). However, this technique suffers from such problems as excessive noise, false positives, requires considerable technical expertise, and relatively expensive instruments and reagents (Walcott et al. J. Food Prot. 54:387–401, 1991).

Prior to the introduction of the automated PCR amplification technique employing the thermostable enzyme Taq DNA polymerase and temperature cycling instruments, a sophisticated method for enhancing the sensitivity of a manual PCR system for detection of human immunodeficiency virus (HIV) was developed which involved appending bacteriophage promoter sequences to one of the priming oligonucleotides for the PCR. This resulted in the generation of amplicons [defined below] which were subsequently transcribed in vitro in the presence of radioisotope-labelled ribonucleotide triphosphates (rNTPs) to give further amplification of the PCR product by production of radioisotope-labelled RNA transcripts (Murakawa e al., 1988, DNA, 7:287–295)). Transcripts incorporating the radioactively labelled ribonucleotides were sensitively analyzed by a complicated procedure involving combined electrophoresis and autoradiography.

Despite the resulting improvement in the sensitivity of PCR, this method would have limited applicability in routine PCR analyses, especially for food industry and other large-scale users, since it is difficult to automate, requires extensive manipulation of the sample in carrying out the amplifications and performing the electrophoretic and autoradiographic analyses of the products, and relies upon the use of a hazardous radioisotope to permit detection of the amplification product. Furthermore, this method does not allow the investigator to quantitatively analyze the product of the reaction (i.e., the method does not provide a quantitative assay of the original target organism) which is sometimes necessary to assess the degree of microbial hazard of a test sample. Thus, while this method provides for some amplification of the HIV PCR products by in vitro transcription in the presence of radioisotope-labelled rNTPs, the process is not practical for use on a routine basis. Indeed, no diagnostic test using this principle has been made available for widespread use to this date, primarily because of the cumbersome nature of the entire procedure. Although it might be supposed that the in vitro transcription technique described above could be re-designed to use non-radioactive (and, hence, non-hazardous) labels (e.g., digoxigenin, biotin, etc.) on the rNTPs for incorporation into the final RNA transcripts, in order to facilitate their subsequent detection in a hybridization reaction, this would still incur additional cost to the test and complicate the preparation of reagents (i.e. the labelled rNTPs). Furthermore, it has been proven that RNA polymerases generally, and T7 RNA polymerase in particular, experience some inhibition when incorporating labelled rNTPs (e.g. digoxigenin-or biotin-rUTP) into RNA transcripts (Heer et al., 1994, BioTechniques, 16:54–55). Thus, the use of such labelled rNTPs for the in vitro transciption of PCR products would diminish the overall efficiency of the reaction.

Accordingly, those concerned with the development and application of PCR-based diagnostic tests have recognized the need for simple, non-hazardous technologies for augmenting the sensitivity of PCR tests. Furthermore, there is a great need for quantitative methods for detecting pathogens, rather than the purely qualitative approaches currently being practised, since it is often necessary to estimate the degree of microbial hazard associated with a sample (e.g., foods) on the basis of the level of contamination.

Therefore, there is a great need for simple and inexpensive methods to augment the sensitivity and reliability of PCR tests, particularly for the forensic sciences, the food industry, clinical applications and other users who must routinely process large numbers of samples containing very few target cells. It is therefore an object of the present invention to provide a method for the transcriptional enhancement of automated PCR tests for specific pathogens without the need for incorporating hazardous radioisotopes or expensive (and potentially unreliable) chemical labels in the nucleotide transcripts to permit their subsequent detection.

A further object of this invention is to provide a very simple and user-friendly detection procedure for the products of the PCR.

Yet another object of this invention is to provide for the quantitative assay of pathogens in a sample by using the combined target nucleotide enhancement method and detection procedure described above.

Definitions

In accordance with the present invention and as used herein, the following terms are defined with the following meanings, unless explicitly stated otherwise.

The term "amplicon" refers to a fragment of DNA or RNA spanned within a pair of annealing primers; this fragment is amplified exponentially by the enzyme DNA polymerase.

The term "transcriptional enhancement" refers to a procedure for significantly enhancing the number of copies of RNA sequences that are complementary to DNA amplicon sequences by transcription of those amplicon sequences into many copies of RNA by using an appropriate RNA polymerase.

The term "transcriptional reaction mix" refers to RNase-free deionized distilled water containing 80 mM Tris-HCl (pH 7.5), 12 mM MgCl$_2$, 4 mM spermidine, 20 mM NaCl, 20 mM dithiothreitol, 1 mM of each rNTP (Promega, No. P1221), 10 units of T7 RNA polymerase (Promega. No. P2075) and 20 units of RNasin (Promega, No. N2511) per 25 µl).

The term "PCR" refers to a DNA polymerase mediated amplification of a given fragment of DNA in a cyclical reaction where the annealing of primers, synthesis of progeny strand DNA and denaturation of the duplexes, each conducted at different temperatures. The polymerase used in this cyclical reaction—Taq polymerase—is an enzyme isolated from *Thermus aquatious* and is stable at high temperatures.

Yet another object of this invention is to provide for the quantitative assay of pathogens in a sample by using the combined target nucleotide enhancement method and detection procedure described above.

As disclosed in detail above, in one embodiment of this invention the combined transcriptional enhancement and immunoenzymatic assay procedure of the present invention can be applied to any instance where one wishes to employ the PCR technique for the assay of a microbe (bacteria, fungi, viruses, etc.) either directly or in an enrichment culture of a sample (e.g., food, clinical specimen, environment, etc.). This application will be particularly useful in the clinical (human medical and veterinary), agricultural (food safety, food industry) and environmental (water systems, soils) fields, where it is often necessary to analyze samples for the presence of minute quantities of target cells (e.g. pathogens), and where the availability of an ultrasensitive and specific method would be particularly advantageous.

In another embodiment, the present system can be applied in the PCR-based genetic analysis of target cells (e.g., organs, tissues, cellular organelles, etc.) or specific genes. This application would enjoy many uses in the medical and biological fields, where it could be used as a tool to aid in the diagnosis of genetic diseases or the characterization of genetic material in biological samples.

In yet another embodiment, the present invention can be applied in the PCR-based analysis of target cells (e.g., microbes, eukaryotic cells, etc.) captured from a test sample on a solid phase (e.g., immunomagnetic beads). This application would be of particular use in the microbiological, biochemical and medical fields, where it is often desirable to analyze for the presence of very low numbers of target cells recovered from large volumes of sample (e.g., environmental water samples, body fluids such as blood, etc.).

Thus, the principle of the present invention should be widely applicable not only to the detection of food pathogens such as *L. monocytogenes*, but also in the analysis of a wide variety of other bacteria, fungi, viruses, etc., of clinical or economic interest.

Definitions

In accordance with the present invention and as used herein, the following terms are defined with the following meanings, unless explicitly stated otherwise.

The term "amplicon" refers to the final DNA product of a nucleic amplification technique employing a pair of annealing primers, wherein one primer includes an RNA polymerase binding sequence fragment; it is the double stranded DNA "spanned" within and including the pair of annealing primers with a functional, double stranded RNA polymerase binding sequence at one end. The orientation of the RNA polymerase binding sequence (eg. T7 promotor) will cause the amplicon to be transcribed by the enzyme RNA polymerase to yield a large number of single stranded RNA complementary copies of the amplicon sequence.

The term "primer" refers to an oligonucleotide which is capable of acting as a point of initiation of synthesis when placed under conditions in which the synthesis of a primer extension product is induced, i.e., in the presence of nucleotides and an agent for polymerization such as DNA polymerase and at a suitable temperature and pH. The primer is single stranded for maximum efficiency in amplification and must be sufficiently long to prime the synthesis of extension products in the presence of the agent for polymerization. The exact lengths of the primers will depend on many factors, including temperature and source.

The term "transcriptional enhancement" refers to a procedure for significantly enhancing the number of copies of RNA sequences that are complementary to DNA amplicon sequences by transcription of amplicon sequences into copies of RNA by using an appropriate RNA polymerase.

The term "transcriptional enhancement product", or "TE product" refers to the RNA sequence products of the amplicon transcription reaction in which an RNA polymerase transcribes the strand of DNA sequence, delimited by the double stranded amplicon. The TE products are multiple copies of single stranded RNA that are complementary to the target nucleic acid sequence, generated in the transcriptional enhancement reaction using an RNA polymerase.

The term "PCR" refers to a DNA polymerase mediated amplification of a given fragment of DNA in a cyclical reaction where the annealing of primers, synthesis of progeny strand DNA and denaturation of the duplexes, are each conducted at different temperatures. The polymerase used in this cyclical reaction—Taq polymerase—is an enzyme isolated from *Thermus aquatious* and is stable at high temperatures.

The term "target nucleic acid sequence" refers to any DNA or RNA sequence that is desired to be detected.

SUMMARY OF THE INVENTION

This method applies to techniques that employ polymerase chain reactions (PCR) to amplify copies of the target DNA or RNA (via reverse-transcriptase PCR) to allow for detection. This method combines the following four steps for the first time: DNA amplicon synthesis and amplification in a modified nucleic acid amplification technique (eg. PCR) using a target nucleic acid sequence as a template; amplicon transcription into RNA sequences with amplification thereof to generate a significantly increased number complementary RNA sequences (i.e., transcriptional enhancement (TE) products); capture of TE products using immobilized complementary DNA sequences; and immunochemical detection of the heteroduplex nucleic acid sequences thereby formed. This method extends standard nucleic acid amplification techniques (eg. PCR) to accommodate transcription of the PCR products into RNA sequences with amplification, to significantly magnify the signal-to-noise ratio of the diagnostic test. This combination of steps results in a new assay with increased simplicity, speed and sensitivity compared to standard nucleic acid detection methods.

FIGURES

FIG. 3 shows the sensitivity of detection of the PCR-generated DNA template by combined transcriptional enhancement and immunoenzymatic assay. Purified 756 bp PCR-generated template DNA from the hly A gene of *L. monocytogenes* was serially diluted in PCR buffer. The dilutions were mixed with TRM, giving different amounts of DNA in each reaction, and then subjected to transcriptional enhancement followed by immunoenzymatic assay as described in the text. The results are presented as mean $A_{450}$±standard deviation (n=3).

DETAILED DESCRIPTION OF THE INVENTION

The method described in this invention applies to techniques that employ polymerase chain reactions (PCR) to amplify copies of target DNA or RNA sequences (via reverse-transcriptase PCR) to allow for their detection. This invention constitutes an extension beyond the prior art rendering nucleic acid sequence detection more feasible and reliable while significantly improving the signal-to-noise ratio of these techniques. This improvement is especially notable in situations where a target nucleic acid sequence is present as a minute component of a mixture of nucleic acid sequences or is present at low levels.

The method of the present invention combines the following four steps for the first time: DNA amplicon synthesis and amplification in a modified PCR using a target nucleic acid sequence as a template; amplicon transcription into RNA and amplification; RNA:DNA hybrid formation: and immunochemical detection of heteroduplex nucleic acid sequences. This method extends the standard PCR techniques to accommodate the amplification of copies of PCR product and transcription into RNA, which, following binding to DNA sequences facilitates immunochemical detection of the RNA:DNA hybrids thereby formed.

Combining the first two steps of this invention uses the DNA products of the PCR reaction as templates to synthesize RNA sequences complementary to the target sequence. This is accomplished by appending RNA polymerase promoter sequences to one of the priming oligonucleotides that will be used to direct the polymerase chain reaction for synthesis and amplification of DNA sequences that are complementary to the target nucleic acid sequence of interest. Thus, a family of DNA sequences that will be produced by PCR that will contain an appropriate RNA polymerase promoter, allowing for an RNA polymerase to be used subsequently to transcribe and further amplify target nucleic acid sequences by synthesizing multiple copies of RNA sequences complementary to the target sequence.

This modified PCR reaction in conjunction with the translation/transcription step performs two functions that serve to enhance the signal-to-noise ratio: the primer nucleotides to which RNA promoter sequences have been appended will effect a selection of signal over noise. The priming nucleotide sequences should only bind to target sequences and therefore will only allow for multiple copies of these sequences which would include the appropriate RNA polymerase promoter sequences. Thus, the non-target sequences should not be translated and amplified by the RNA polymerase, since only the DNA sequences containing the RNA polymerase promoter sequences will be recognized by the RNA polymerase.

In the third step of this invention, RNA:DNA hybrid formation, advantage is taken of the fact that DNA has been transcribed into RNA, allowing the target nucleic acid sequences to once again be selected out of background nucleic acid sequences by hybridizing the RNA sequences to complementary DNA probes attached to a solid support, to generate immobilized RNA:DNA hybrids. This allows for washing away of extraneous material.

The heteroduplex nature of the nucleic acids sequences allows for the use of antibodies that specifically recognize RNA:DNA hybrids and can be used to detect the hybrids in one of many immunochemical methods of analysis. This antibody can possess a chemical group allowing for direct detection of the hybrids, or it can also be detected indirectly using another antibody to which a chemical group is attached, that recognizes the anti-RNA:DNA antibody.

Sample Preparation

In one particular embodiment, the sample to be tested is typically a piece of food, for example meat or cheese, or another source containing principally double stranded nucleic acids. This includes microorganisms and/or other cellular material associated with these samples. The test sample is first treated to release the nucleic acids from the cells, followed by a step to denature the nucleic acids. This is typically accomplished by lysing the cells in a lysis buffer solution and the denaturation of nucleic acids is preferably accomplished by heating the resulting solution in boiling water or alkali treatment (e.g., 0.1N sodium hydroxide). The denaturing step can often be used simultaneously with the lysis method. The release of nucleic acids can, also, be obtained through mechanical disruption such as freezing/thawing, abrasion, sonication, physical/chemical disruption (eg. polyoxyethylene ether detergents like Triton®, polyoxytheylenesorbitan detergents like Tween®, sodium dodecylsulfate, alkali treatment, osmotic shock, heat, or lysing using enzymes such as proteinase K, lysozyme, pepsin). The resulting medium will contain nucleic acids in single stranded form which is then assayed according to present hybridization methods (Wang et al., Appl. Environ. Microbiol., 1992).

When the sample contains free single-stranded nucleic acid sequences, the sample is in proper form for PCR. When the assay is performed for detection of a microorganism, a bacterium for example, the cells must be lysed and the nucleic acids have to be exposed in order to be available for hybridization with the priming oligonucleotides. Methods of lysis have been previously described and are well known to one skilled in the art.

DNA Amplicon Synthesis and Amplification in a Modified PCR

Target DNA is amplified by a modified PCR procedure, or RNA is amplified by a modified reverse transcriptase PCR, using an oligonucleotide primer pair complementary to specific nucleotide sequences on the two strands of the target nucleic acids, in which one of the primers has appended at its 5' end a suitable promoter sequence that will be recognized by an appropriate RNA polymerase (e.g. bacteriophage T7 RNA polymerase) in a subsequent step designed to further amplify the PCR product by transcription. For this reaction, primer sequences are chosen which are complementary to unique nucleic acid sequences found solely in the pathogen or gene of interest (e.g. the hly A gene of *Listeria monocytogenes*). Primers will normally be 15–30 nucleotides in length (not including appended promoter sequences) and have greater than 30% G+C content in order to give optimum PCR amplification. Any primer sequences suitable for conventional PCR amplification will normally be suitable for the present reaction. Since the appended promoter sequences do not participate in the initial base-pairing of the primer to complementary sequences on the target nucleic acid, their presence will normally not affect the PCR amplification reaction. The promoter sequences chosen should be as short as possible (e.g. 26 nucleotides or shorter) and should contain all of the necessary information to allow binding of RNA polymerase and efficient initiation of transcription. Examples of suitable promoter sequences are the bacteriophage T7 and SP6 RNA polymerase binding and transcription initiation sequences.

Amplicon Transcription into RNA and Amplification to Generate TE Product

Once DNA amplicon synthesis has been achieved by a modified PCR to produce an amplicon containing a functional, double stranded RNA promoter at one end, the amplicon is then converted into many copies of complementary RNA by transcription using an appropriate RNA polymerase and all of the required rNTPs. For example, amplicons sythesized using a primer pair in which one of the primers contains bacteriophage T7 promoter sequences appended at its 5' end are subjected to a transcription reaction using bacteriophage T7 RNA polymerase. In this reaction, it is necessary to utilize an RNA polymerase which is specific for the promoter sequences appended to the primer used in the initial PCR.

RNA:DNA Hybrid Formation

Multiple copies of an appropriate DNA probe are generated using the PCR procedure as described above. In general, the same pair of oppositely oriented oligonucleotide primers are used that were used for the amplicon synthesis in the modified PCR step—minus the appended RNA polymerase promoter sequences. These primers are synthesized using standard techniques, including automation, that are well known in the art.

Template DNA will be substantially similiar to a region of the target DNA or complementary to target RNA sequences to allow for efficient binding of the transcribed amplicons. The choice and design of the oppositely oriented oligonucleotide primers will determine the sequence of DNA generated during PCR.

Polymerase chain reaction method will be used to generate repeated in vitro replication of target nucleic acid sequences bounded by these oppositely oriented primers. Manufacturer's instructions that accompany DNA synthesizers will direct the method of PCR to generate multiple copies of the target nucleotide sequence probes.

Once the PCR method has generated an appropriate number of copies of the target nucleic acid sequences of interest, the PCR products will be digested using an appropriate restriction endonuclease (eg. Hind III) to cleave off the primer-complementary sequences, leaving target-complementary nucleic acid sequences for use as DNA probes. These probes will be sufficiently long (typically greater than 16 nucleotides) and sufficiently complementary to the target nucleic acid sequences to allow for efficient binding of transcribed amplicons to generate RNA:DNA hybrids.

The DNA probes thereby created can be attached to solid supports such as microtiter wells, "dip sticks", or macroporous polyester cloth. Modes of DNA sequence attachment to various forms of solid supports are well known in the art. The primary objective of the mode of attachment chosen is to allow for secure attachment of the DNA to the support while allowing for future efficient binding of complementary RNA sequences.

The probe may be denatured by heating and then diluted in ice-cold coating buffer. The solid support may be incubated with this coating buffer, air dried, and DNA cross-linked to the solid support, for example by exposure to ultraviolet light for an appropriate amount to time to allow for efficient cross-linking. The solid support may be washed with appropriate buffer and nonspecific attachment sites blocked by incubation with hybridization solution, including protein blocking reagent, following by washing, air-drying, and storage under appropriate conditions until use [see P. Tijssen, "Practice and Theory of Enzyme Immunoassays in R. H. Burton and A. H. van Knippenberg, eds., 15 Laboratory Techniques in Biochemistry and Molecular Biology, (New York, Elsevier Publication 1985) at 549].

Immunochemical Detection of Heteroduplex Nucleic Acid Sequences

The RNA products of the amplicon transcription reaction are hybridized with a complementary DNA probe immobilized on a solid phase, and the resulting RNA:DNA hybrids are detected immunochemically using an antibody that recognizes the RNA:DNA hybrids. Such anti-RNA:DNA antibodies recognize and bind to the unique helix structure formed whenever RNA and DNA strands base-pair with each other, regardless of the specific nucleotide sequence of the hybridizing strands. Thus, the anti-RNA:DNA hybrid antibody will be useful in the immunochemical assay of any amplicon transcription product, provided that a suitable complementary DNA probe is available for immobilization on the solid phase. The solid phase used for the immobilization of the DNA probe can be any suitable surface which will enable the binding of DNA by either covalent or non-covalent bonds, including, but not limited to, plastic microtiter plates, microporous membranes of nylon or nitrocellulose, hydrophobic cloths, immunomagnetic beads, etc. The immobilized DNA is any DNA segment in the single stranded form which is complementary to the amplicon transcription reaction product, but which does not contain sequences complementary to the priming oligonucleotides used in the initial modified PCR. Thus, the immobilized DNA can be created by isolation of a specific DNA fragment generated by restriction digestion, by PCR amplification of sequences internal to the amplicon used in the transcription reaction, or by synthesizing an oligonucleotide using synthetic chemistry processes. DNA fragments originally in the double stranded form can be rendered single stranded by denaturation (e.g. heating, alkali) prior to immobilization on the solid phase. In the immunochemical detection system, the RNA:DNA hybrids formed on the solid phase by reaction of the amplicon transcription product with the immobilized DNA are detected by reaction with an anti-RNA:DNA hybrid antibody which is labelled with a detectable chemical moiety (e.g. enzyme, fluorophore, etc.). Alternatively, an unlabelled anti-RNA:DNA hybrid antibody can be used, followed by detection of the antibody using a second anti-antibody labelled with a detectable chemical moiety.

The present invention will now be illustrated, but is not intended to be limited, by the following examples.

EXAMPLE 1

Assay for the Detection of L. monocytogenes

As examples of the applicability of this transcriptional enhancement and immunoenzymatic assay system in automated PCR analyses, the amplification and detection of hlyA gene sequences encoding the virulence factor listeriolysin O possessed by the well-known food pathogen Listeria monocytogenes is demonstrated.

Sample Preparation

Bacteria used in this study included two Listeria monocytogenes reference strains (non-haemolytic type strain ATCC 15313 and ATCC 43256) and 11 L. monocytogenes isolates from egg, dairy and environmental samples collected by Canadian Government inspection staff and submitted for routine microbiological analysis by Laboratory Services Division, Agriculture and Agri-Food Canada. Unless otherwise stated, experiments were routinely carried out using an L. monocytogenes isolate from cheese. Other Listeria spp. examined include 3 strains of L. innocua, 2 strains of L. ivanovii, 2 strains of L. seeligeri and 1 strain each of L. welshimeri, L. murrayi and L. grayi. Additionally, several Gram-positive and Gram-negative non-Listeria organisms were examined, including: Streptococcus thermophilus (ATCC 19258), Lactobacillus casei (ATCC 393), lactococcus lactis (ATCC 19257), Micrococcus luteus (ATCC 9341), Enterococcus faecalis (ATCC 19433), Staphylococcus epidermidis (ATCC 12228), Bacillus cereus (ATCC 14579), Bacillus subtilis (ATCC 6051), Pseudomonas aeruginosa (ATCC 10145), Escherichia coli (ATCC 11775), Salmonella typhimurium (strain LT2)(ATCC 19585) and Yersinia enterocolitica (ATCC 9610). All bacteria were routinely grown by inoculating a single colony from Brain Heart Infusion (BHI)(Difco) agar into Trypticase Soy Broth (TSB)(BDH) and shaking for 24 h at 30° C. for Listeria, Lactococcus, Micrococcus, Bacillus and Yersinia spp., and at 37° C. for all other bacteria. Viable counts were obtained by plating serial dilutions of the broth cultures on BHI agar.

Bacterial lysates of broth cultures and purified chromosomal DNA were prepared for the PCR as previously described (Blais and Phillippe, 1993, Appl. Environ. Microbiol., 59:2795–2800).

PCR For Use in DNA Amplicon Synthesis and Amplification in a Modified PCR and in RNA:DNA Dimer Formation Primers for the PCR were selected from the published nucleotide sequence of the hlyA gene (Mengaud et al., 1988, Infect. Immun., 56:766–772). A 730 bp fragment spanning nucleotides 602 to 1332 (encompassing the two Hind III sites) was amplified using a 21-mer forward primer 5'-CATTAGTGGAAAGATGGAATG-3' (primer A) and a 20-mer reverse primer 5'-GTATCCTCCAGAGTGATCGA-3' (primer B). Oligonucleotides were synthesized on a DNA synthesizer (Applied Biosystems, model 391, PCR-mate-EP), using phosphoramidite chemistry (Applied Biosystems) according to the manufacturer's instructions. For the PCR, 10 $\mu$l of the bacterial lysate prepared from broth suspensions were added to 89.5 $\mu$l of PCR mixture containing 0.22 mM of each dNTP, 1.1 $\mu$M each of the forward and reverse primers, 2.2 mM $MgCl_2$, 55 mM KCl, 11 mM Tris-HCl (pH 8.3) and 0.11% (w/v) Triton X-100™. The mixtures were then overlaid with mineral oil, placed in a thermal cycler (Perkin-Elmer Cetus, model TC 480) and held at 80° C. for 10 min before adding 0.5 $\mu$l containing 2 units of Taq DNA polymerase (Perkin-Elmer Cetus). The reaction mixture was then subjected to 30 cycles of denaturation at 94° C. for 1 min, primer annealing at 55° C. for 1 min, and primer extension at 72° C. for 2 min. An additional 2 min was given for completion of primer extension after the last cycle. Amplicons were then analyzed by electrophoresis of 10 $\mu$l of PCR product in a 1.2% agarose gel at 100 V for about 1.5 h, followed by staining for 20 min in a 10 $\mu$g/ml ethidium bromide solution. DNA on the gels was visualized by fluorescence under UV light and photographed on Polaroid 667 film. The size of the amplicon was determined by including a sample of 123 bp ladder DNA molecular size marker (Gibco BRL, No. 5613SA) in each gel.

DNA Amplicon Synthesis and Amplification in a Modified PCR

The PCR was performed as above, except that the forward primer was replaced with an identical oligonucleotide having an additional 26 nucleotides corresponding to the T7 RNA polymerase promoter sequences appended to the 5'-end, giving the 47-mer forward primer 5'-AATTTAATACGACTCACTATAGGGATCATTAGTGG AAAGATGGAATG-3' (primer A-T7). [The T7 RNA polymerase binding and preferred transcriptional initiation sites are indicated in bold]. Use of this primer in combination with the reverse primer B yielded a 756 bp amplicon (see Blais 1994 Applied and Environmental Microbiology 60 348).

Amplicon Translation into RNA by Transcription and Amplification

The DNA amplicons containing T7 RNA polymerase promoter sequences were transcribed by T7 RNA polymerase as follows: 25 $\mu$l of PCR product were mixed with 25 $\mu$l of transcription reaction mix (TRM; RNase-free deionized distilled water containing 80 mM Tris-HCl (pH 7.5), 12 mM $MgCl_2$, 4 mM spermidine, 20 mM NaCl, 20 mM dithiothreitol, 1 mM of each rNTP (Promega, No. P1221), 10 units of T7 RNA polymerase (Promega, No. P2075) and 20 units of RNasin (Promega, No. N2511) per 25 $\mu$l), and incubated at 37° C. for 2 h. The product was then analyzed by subjecting 10 $\mu$l of the mixture to agarose gel electrophoresis, or by immunoenzymatic assay on a microtiter plate as described below.

RNA:DNA Hybrid Formation

Probe DNA was prepared and immobilized on a microtiter plate as follows. An hlyA-specific DNA capture probe for the immunoenzymatic assay of the amplicon transcription product was prepared by PCR using primers A and B and 10 ng of purified L. monocytogenes chromosomal DNA as template. The 730 bp PCR product was digested with Hind III to give a 657 bp fragment devoid of primer-complementary sequences. This fragment (probe DNA) was purified on Magic PCR Preps™ columns (Promega, No. A7170) and stored as a 1 µg/µl stock in deionized distilled water at −20° C. The wells of a microtiter plate (Dynatech Laboratories, Inc., No. 011-010-3350) were coated with probe DNA by the following method: the probe DNA was denatured by heating at 100° C. for 10 min and then diluted to 2 µg/ml in ice-cold coating buffer (0.3M Tris-HCl, pH 8.0, containing 0.5M $MgCl_2$ and 1.5M NaCl). Microtiter plate wells were incubated with 100 µl of this coating buffer solution containing 0.2 µg of probe DNA at 37° C. for 16 h. The wells were emptied and air-dried, followed by cross-linking of the DNA by exposure to ultraviolet light (254 nm) for 3 min. They were then washed 3× with wash buffer (0.1M Tris-HCl, pH 8.0, containing 2 mM $MgCl_2$, 1M NaCl and 0.1% (v/v) Tween20™), and blocked by incubation with 100 µl of hybridization solution (5× SSC [1× SSC is 0.15M NaCl plus 0.015M sodium citrate], 1% (w/v) protein blocking reagent, 0.1% ((w/v) N-lauroylsacosine, and 0.02% (w/v) sodium dodecyl sulfate) at 37° C. for 1 h. The wells were then washed 3× with 0.01M phosphate-buffered (pH 7.2)/0.85% NaCl (PBS) containing 0.05% (v/v) Tween20™ (PBST) and air-dried, and the plate (probe DNA-plate) was stored sealed at 4° C. until use.

RNA products of the amplicon transcription reaction were bound to immobilized DNA sequences as follows. Fifty µl samples of amplicon transcription product were mixed with 50 µl of hybridization solution containing 50% (v/v) formamide in the wells of a probe DNA-plate. The plate was then incubated at 56° C. for 1 h, followed by washing with PBST as above. Subsequent reactions were carried out at room temperature.

Immunochemical Detection

To detect RNA:DNA hybrids formed on the plate a goat anti-RNA:DNA IgG antibody was prepared according to the method of Stollar and Rashtchian (1987, Anal. Biochem., 161:387–394 herein incorporated by reference). The wells were incubated with 100 µl of goat anti-RNA:DNA IgG (16) at 5 µg/ml in PBST containing 0.2% (w/v) protein blocking reagent (PBST-B) for 20 min, then washed with PBST, followed by a further 20 min incubation with 100 µl of anti-goat IgG-peroxidase conjugate (Sigma, No. A-3540) diluted 1:2000 in PBST-B. After a final wash with PBST, the wells were incubated with 100 µl of TMB microwell peroxidase substrate system (Kirkegaard and Perry Laboratories, Inc., No. KP-50-76-00) for 20 min. The reaction was stopped by the addition of 50 µl of 1M $H_2SO_4$, and the absorbance in the wells was measured at 450 nm using a scanning microtiter plate autoreader (Bio-Tek Instruments, Model EL900).

Time-course of the transcriptional enhancement reaction

Figure 1:
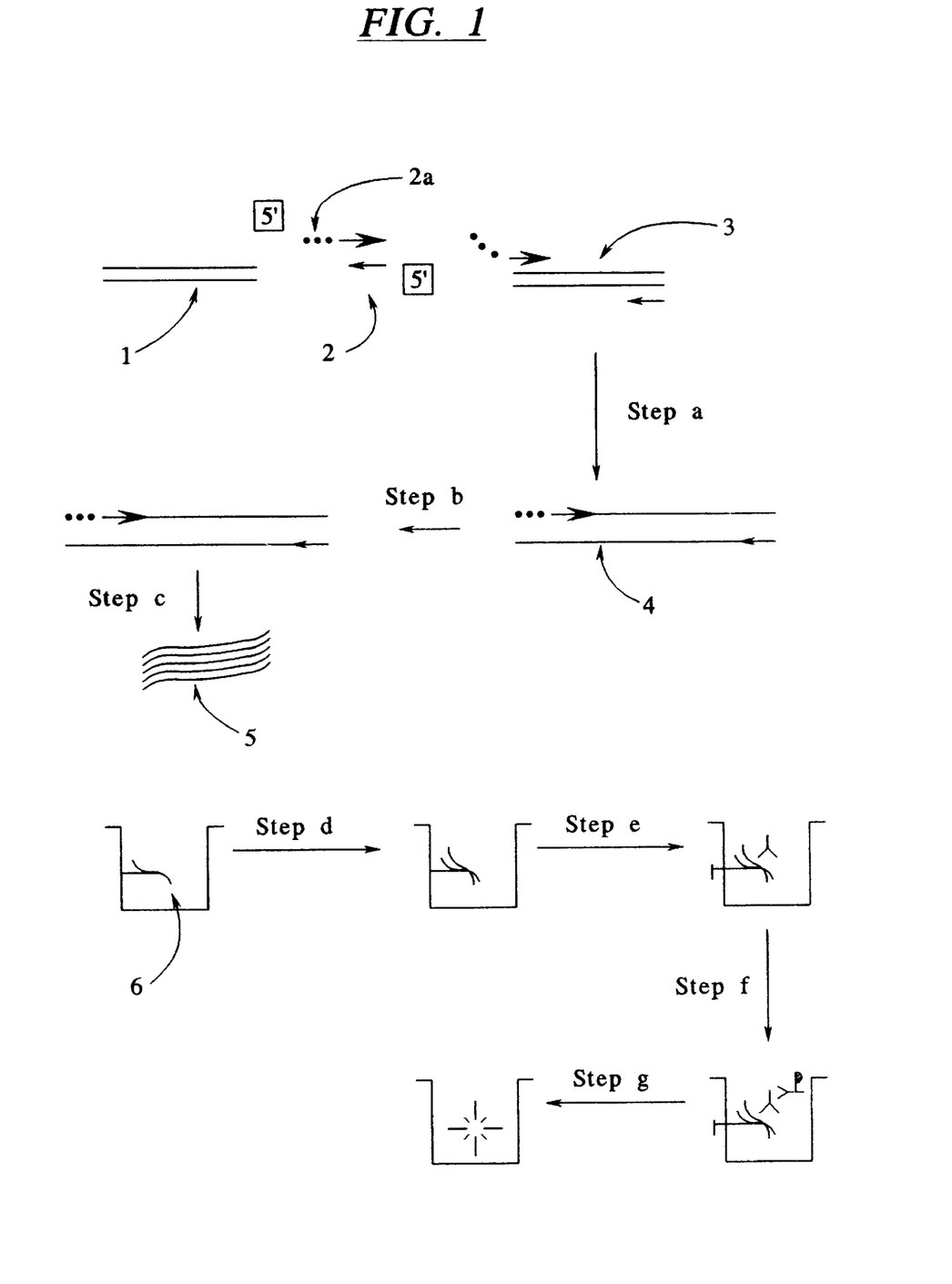
FIG. 1 is a schematic diagram of the transcriptional enhancement and immunoenzymatic assay methods showing the mechanism of the combined PCR and transcriptional enhancement reactions starting with a double stranded DNA target sequence (1), and the mechanism of hybridization of the RNA transcripts with probe DNA immobilized in a microtiter plate well followed by immunoenzymatic detection of the RNA:DNA hybrids formed (2).
Figure 2:
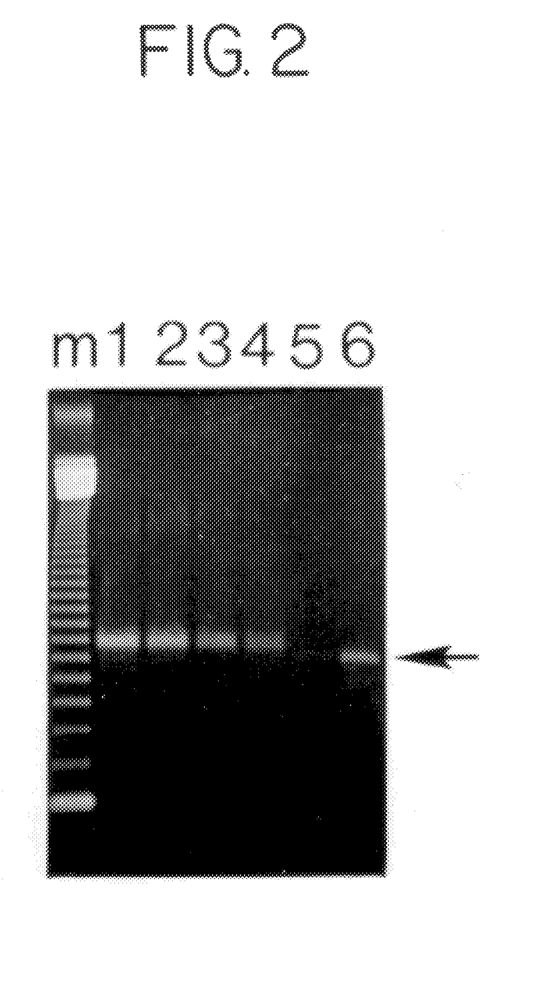
FIG. 2 is a copy of a photograph of an agarose gel electrophoresis experiment in which the RNA transcripts from the transcriptional enhancement reaction have been separated, and shows the effect of varying the incubation time on the amount of transcript produced. The optimum reaction time for transcriptional enhancement of PCR-amplified hly A sequences from *Listera monocytogenes* is demonstrated. Twenty-five μl of PCR buffer containing 0.1 μg of purified 756 bp template DNA were mixed with 25 μl of TRM (Transcription Reaction Mixture)and incubated at 37° C. for various periods of time, and 10 ul of product were analyzed by electrophoresis on a 1.2% agarose gel as described in the text. Incubation times: lane 1, 3 h; lane 2, 2 h; lane 3, 1 h; lane 4, 0.5 h; lane 5, 0 h. Lane m, 123 bp ladder DNA marker; Lane 6, 0.07 μg of 756 bp template DNA (arrow).

The optimum reaction time for the transcriptional enhancement of a 756 bp DNA template generated by PCR amplification of hlyA sequences using primers A-T7 and B was determined by incubating a fixed quantity of the PCR DNA with transcription reaction mix (TRM hereinafter as defined above) for various periods of time. FIG. 2 shows that the product of the transcription reaction obtained at all incubation times (FIG. 2, lanes 1–4) was of a uniform size, suggesting that the transcripts were complete. The amount of transcript produced increased with the incubation time, with maximum production (as judged by the intensity of the transcript bands in the agarose gel) occurring after 2–3 h incubation with the TRM (FIG. 2, lanes 1 and 2). No qualitative difference in the amount of transcript produced was discernable after 3 h incubation. These experiments show that a 2–3 h incubation is sufficient to produce maximum transcription of the DNA template (PCR product).

The specificity of initiation of the transcription reaction at the T7 promoter sequences was confirmed by incubation of the TRM with 0.1 µg of a 730 bp amplicon (devoid of the T7 promoter sequences) generated by PCR amplification of hlyA sequences using primers A and B. No detectable transcript was produced after a 2 h incubation, showing the necessity for incorporating a functional T7 promoter in the PCR product to enable its use as a template for the transcription reaction.

Comparative sensitivity of the transcriptional enhancement reaction

The improvement in the sensitivity of detection of *L. monocytogenes* cells by transcriptional enhancement (as defined above) of the PCR product was studied using (a) agarose gel electrophoresis analysis of the amplification products, and (b) hybridization of the TE reaction products with hlyA probe DNA immobilized in the wells of a microtiter plate and subsequent immunoenzymatic assay employing an anti-RNA:DNA antibody. Table 1 shows that the limit of detection for *L. monocytogenes* cells was essentially the same (ca. 1000 cells) when hlyA sequences were amplified by PCR using both primer sets A, B (730 bp product) and A-T7, B (756 bp product) and the products analyzed by agarose gel electrophoresis. When the PCR product obtained using primers A-T7 and B was subjected to the TE reaction, the RNA transcript from as few as 185 cells could be visualized on the gel (Table 1). No evidence of the 756 bp PCR DNA could be discerned at this level of cells. A minimum of 10–12 ng of purified 730 bp and 756 bp PCR DNA could be visualized on a gel, whereas transcriptional enhancement product from a minimum of 1.2 ng of 756 bp DNA could be visualized on the same gel. Thus, transcriptional enhancement of the PCR and analysis of the products by agarose gel electrophoresis increased the sensitivity ca. 5-fold for the detection of *L. monocytogenes* cells and ca. 8–10-fold for the detection of purified 756 bp PCR DNA.

TABLE 1

Comparative sensitivity of PCR-based methods using agarose gel electrophoresis analysis[a].

| Detectability Primers | Transcriptional Enhancement | (cells) |
| --- | --- | --- |
| A, B | No | 980 ± 185 |
| A-T7, B | No | 1090 ± 210 |
| A-T7, B | Yes | 185 ± 50 |

[a]Serial dilutions of *L. monocytogenes* cells in TSB were subjected to PCR amplification using various sets of primers as indicated. The PCR product was then analyzed by agarose gel electrophoresis before and after transcriptional enhancement as described in the text. Detectability is reported as the minimum number of cells per reaction giving a visible product (mean ± standard deviation; n = 3).

Figure 3:
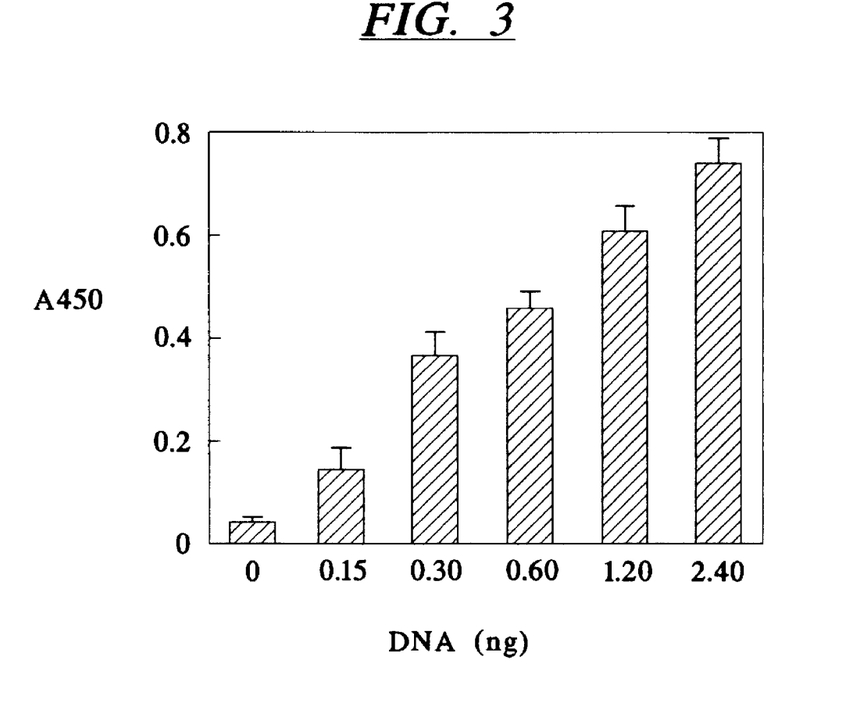
FIG. 3 is a bar graph depicting the quantitative response of the immunoenzymatic assay when different amounts of PCR-generated template DNA were subjected to the combined transcriptional enhancement and immunoenzymatic assay procedure.

The detection of transcriptional enhancement reaction product by hybridization with an hlyA DNA probe immobilized in the wells of a microtiter plate and immunoenzymatic assay of the resulting RNA:DNA hybrids using an anti-RNA:DNA detector antibody was studied. The presence of as little as 0.15 ng of purified 756 bp PCR DNA in the TE reaction gave a detectable response (absorbance at 450 nm) above the background (no DNA) in the immunoenzymatic assay of the TE product (FIG. 3). This represents a 10-fold improvement in the overall sensitivity of the procedure as compared to analysis of the product by agarose gel electrophoresis. The specificity of this assay was confirmed by omitting the 756 bp PCR DNA from the transcriptional enhancement reaction and adding either 0.1 µg of purified bacteriophage lambda DNA (Boehringer Mannheim, No.

Figure 4:
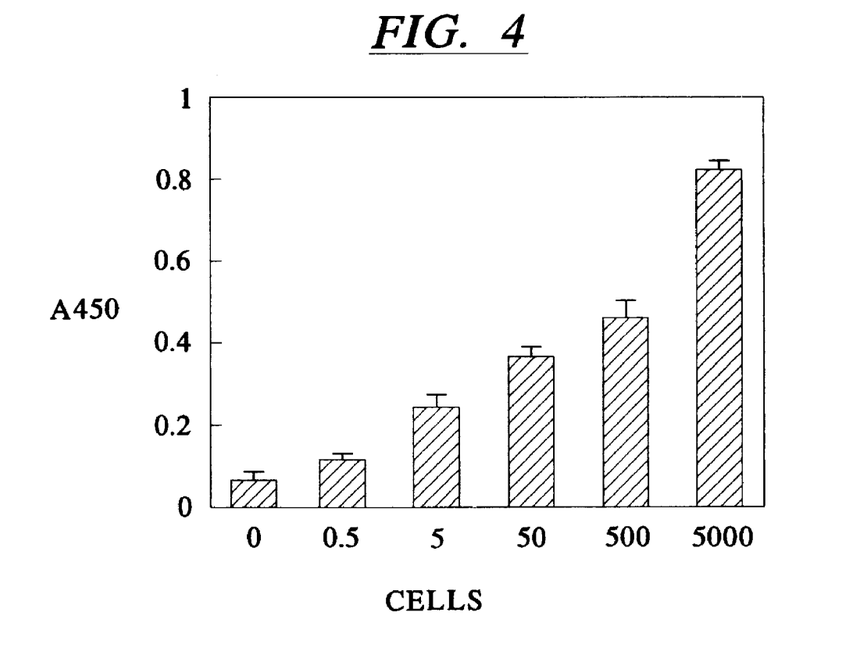
FIG. 4 is a bar graph depicting the sensitivity of the quantitative response of the immunoenzymatic assay when different amounts of target *L. monocytogenes* cells were subjected to the methods described in this invention. Varying numbers of *L. monocytogenes* cells suspended in TSB were subjected to PCR amplification using hlyA gene-specific primers A-T7 and B. The PCR product was then transcriptionally enhanced and processed in the immunoenzymatic assay as described in the text. The results are presented as mean $A_{450}$±standard deviation (n=3).

236 250) or 0.1 μg of 16S and 23S *Escherichia coli* rRNA (Boehringer Mannheim, No. 206 398). No detectable response was observed in either instance, indicating that the non-specific DNA or RNA in the sample did not form the necessary RNA:DNA hybrids with the immobilized hlyA probe DNA. When this combined transcriptional enhancement and immunoenzymatic system was applied in the assay of PCR-generated hlyA sequences from whole *L. monocytogenes* cells, a detectable assay response was obtained with fewer than 5 cells added to the initial PCR mixture (FIG. 4). This represents a minimum 200-fold improvement in sensitivity over performing the PCR without applying the transcriptional enhancement and immunoenzymatic detection system of the present invention (Table 1).

Specificity of the transcriptional enhancement reaction

The specificity of this system for *L. monocytogenes* was preliminarily examined by its application to the assay of a small number of different Listeria and non-Listeria organisms. Broth cultures of the different bacteria containing ca. $5 \times 10^8$ cells per ml were lysed and then subjected to PCR using primers A-T7 and B, followed by transcriptional enhancement of the product and immunoenzymatic assay. Table 2 shows that all of the *L. monocytogenes* isolates tested (including two ATCC strains) and none of the other Listeria species gave a strong response (absorbance at 450 nm) in the assay. None of the non-Listeria organisms tested (see Bacterial strains) produced a detectable response in this assay. This demonstrates that the combined transcriptional enhancement and immunoenzymatic detection system utilizing *L. monocytogenes*—specific primers in the initial PCR was specific for this pathogen.

TABLE 2

Specificity of combined transcriptional enhancement of PCR-generated hly A DNA and immunoenzymatic assay for Listeria spp.

| Organism | Origin/source | $A_{450}$[a] |
|---|---|---|
| L. monocytogenes | ATCC 15313 | 1.50 ± 0.08 |
| L. monocytogenes | ATCC 43256 | 1.23 ± 0.15 |
| L. monocytogenes | cheese | 1.38 ± 0.17 |
| L. monocytogenes | cheese | 1.30 ± 0.11 |
| L. monocytogenes | cheese | 1.11 ± 0.09 |
| L. monocytogenes | egg | 1.55 ± 0.10 |
| L. monocytogenes | egg | 1.46 ± 0.16 |
| L. monocytogenes | cream | 1.35 ± 0.10 |
| L. monocytogenes | environmental | 1.30 ± 0.09 |
| L. monocytogenes | environmental | 1.25 ± 0.09 |
| L. monocytogenes | environmental | 1.23 ± 0.12 |
| L. monocytogenes | environmental | 1.16 ± 0.10 |
| L. monocytogenes | environmental | 1.25 ± 0.21 |
| L. innocua | HPB[b] | 0.08 ± 0.02 |
| L. innocua | HPB | 0.06 ± 0.02 |
| L. innocua | cheese | 0.06 ± 0.01 |
| L. ivanovii | HPB | 0.04 ± 0.0 |
| L. ivanovii | ATCC 19119 | 0.06 ± 0.01 |
| L. seeligeri | HPB | 0.09 ± 0.02 |
| L. seeligeri | cheese | 0.09 ± 0.01 |
| L. welshimeri | HPB | 0.08 ± 0.01 |
| L. murrayi | HPB | 0.05 ± 0.02 |
| L. grayi | HPB | 0.04 ± 0.0 |

[a]Mean $A_{450}$ ± standard deviation (n = 2).
[b]HPB, Health Protection Branch, Health and Welfare Canada, Ottawa, Canada.

Operation of preferred embodiments

The above examples demonstrate that it is possible to significantly increase the sensitivity of an automated PCR method for the detection of *L. monocytogenes* by transcriptional enhancement of an amplicon incorporating bacteriophage T7 promoter sequences. The sensitivity was further greatly increased by hybridization of the RNA transcript with a DNA probe immobilized in a microtiter plate followed by immunoenzymatic assay of the RNA:DNA hybrids. This method of detecting the RNA transcript was also simpler to perform than the cumbersome agarose gel electrophoresis approach. Thus, the examples hereinabove prove that a key feature of this method is the combining of the transcriptional enhancement reaction with hybridization of the product with an immobilized DNA probe followed by immunoenzymatic assay using an anti-RNA:DNA antibody. This provided maximum sensitivity and ease of detection of the amplified product. The fact that, unlike other nucleic acid detection systems, the immunoenzymatic assay of the present invention obviates the need for introducing special detector labels (e.g., radioisotopes, biotin, etc.) into either of the hybridizating nucleic acids in the detection system is a great advantage in terms of the simplicity and economy of applying the transcriptional enhancement principle in a routine diagnostic setting (e.g., the food industry). Furthermore, it is well known by those skilled in the art that enzymatic synthesis of nucleic acid strands (RNA or DNA) by incorporation of nucleotides containing detector labels, such as the synthesis of biotin-labelled RNA from a DNA template by an RNA polymerase, can result in uncertain efficiency of the synthetic reaction and variability in the quality of the labelled product. Since the method of the present invention does not require the incorporation of labelled nucleotides of the hybridizing nucleic acid strands, the amplification reaction always operates at maximum efficiency and consistently produces a good quality product for optimum immunochemical detection. The higher sensitivity achieved will permit the detection of *L. monocytogenes* at lower cell densities in enrichment broth during cultivation of this organism from foods and other samples, reducing the total time for the analysis.

On the basis of the number of different strains tested, the detection system demonstrated in the examples hereinabove was specific for the well-known food pathogen *L. monocytogenes*. This system offers two junctures at which the specificity of the test is potentially assured: (i) annealing of the priming oligonucleotides with the target DNA, (ii) hybridization of the transcriptional enhancement product with the probe DNA. The specificity of the system can, of course, be tailored for any particular pathogen, or DNA sequence, by simply designing appropriate oligonucleotide primers for the PCR, and a DNA probe for hybridization with the transcriptional enhancement product.

In the present experiments, probe DNA for the microtiter plate hybridization reaction was prepared by PCR amplification of hlyA sequences and removal of primer-complementary DNA using Hind III digestion of the amplicon, in order to preclude the possibility of formation of RNA:DNA hybrids on the plate due to the possible occurrence of "primer-dimer" by-products during the PCR stage of the test. An alternative approach could involve amplification of internal hlyA sequences using a different set of priming oligonucleotides. Using this strategy, probe DNA for virtually any nucleotide sequence of interest can be readily prepared.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims. presence of very low numbers of target cells recovered from large volumes of sample (e.g., environmental water samples, body fluids such as blood, etc.).

Thus, the principle of the present invention should be widely applicable not only to the detection of food pathogens such as *L. monocytogenes*, but also in the analysis of a wide variety of other bacteria, fungi, viruses, etc., of clinical or economic interest.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

The embodiments of the invention in which an exclusive property or privilege is claimed are defined as follows:

1. A method of nucleic acid sequence detection comprising the steps:
   a) synthesizing DNA amplicons complementary to target nucleic acid sequence by a nucleic acid amplification procedure using one or more pairs of priming oligonucleotides, one of each said pair comprising an RNA polymerase promoter sequence;
   b) transcribing and amplifying said DNA amplicons into transcription enhancement product using an RNA polymerase;
   c) capturing transcription enhancement products by forming RNA:DNA hybrids with an immobilized DNA probe; and
   d) detecting the transcription enhancement product:capture probe complexes immunochemically using antibodies which are reactive with RNA:DNA hybrids.

2. A method as claimed in claim 1, wherein the nucleic acid amplification procedure is polymerase chain reaction.

3. A method as claimed in claim 1, wherein the RNA polymerase and promoter sequence are T7.

4. A method as claimed in claim 3, wherein the T7 RNA polymerase promoter sequence is:
5'-AATTAATACGACTCACTATAGGGAT-3'.

5. A method as claimed in claim 1, wherein the DNA probe is immobilized on a macroporous polyester cloth.

6. A method as claimed in claim 1, directed towards the detection of *Listeria monocytogenes, L. innocua, L. ivanovii, L. seeligeri, L. welshimeri, L. murrayi, L. grayi, Streptococcus thermophilus, Lactobacillus casei, Lactococcus lactis, Micrococcus luteus, Enterococcus faecalis, Staphylococcus epidermidis, Bacillus cereus, Bacillus subtilis, Pseudomonas aeruginosa, Escherichia coli, Salmonella typhimurium,* or *Yersinia enterocolitica*.

* * * * *